United States Patent [19]
Lambert

[11] Patent Number: 5,962,795
[45] Date of Patent: Oct. 5, 1999

[54] SERVICEABLE MEASURING DEVICE

[75] Inventor: Dale J. Lambert, Metairie, La.

[73] Assignee: Thompson Equipment Company, Inc., Jefferson, La.

[ * ] Notice: This patent is subject to a terminal disclaimer.

[21] Appl. No.: 09/035,669

[22] Filed: Mar. 5, 1998

Related U.S. Application Data

[63] Continuation of application No. 08/808,210, Feb. 28, 1997, Pat. No. 5,844,152.

[51] Int. Cl.$^6$ .......................... G01N 11/16; G01N 11/00
[52] U.S. Cl. ........................ 73/866.5; 73/54.41
[58] Field of Search .................. 73/866.5, 54.14, 73/54.32, 54.33, 54.34, 53.03, 53.06, 54.01, 54.41, 886.5, 54.28

[56] References Cited

U.S. PATENT DOCUMENTS 5,686,660  11/1997  Lundberg .............................. 73/54.24

*Primary Examiner*—Hezron Williams
*Assistant Examiner*—Jay L. Politzer
*Attorney, Agent, or Firm*—Raymond G. Areaux; Lisa Charouel

[57] ABSTRACT

A measuring device which maximizes the surface area of a blade transducer, which is swingably coupled to a probe member, and utilizes the force of the medium, such as a slurry, flowing in an in-service pipeline to swingably align the blade transducer in a desired measuring position. The swingable coupling of the blade transducer to the probe member provides for the retraction from and insertion into the medium flowing in the in-service pipeline for repairs, replacement, or sanitization or other maintenance or servicing of such blade transducer, without shutting down the pipeline and related processes, without compromising the integrity of or disturbing the connection (sealed, flanged, welded or otherwise) between the measuring device and the transducer port in such pipeline and significantly minimizing the environmental exposure of the medium. Moreover, the retractability feature of the swingable blade transducer enables other components of the measuring device to be replaced, repaired and sanitized or otherwise maintained or serviced, as desired.

12 Claims, 14 Drawing Sheets

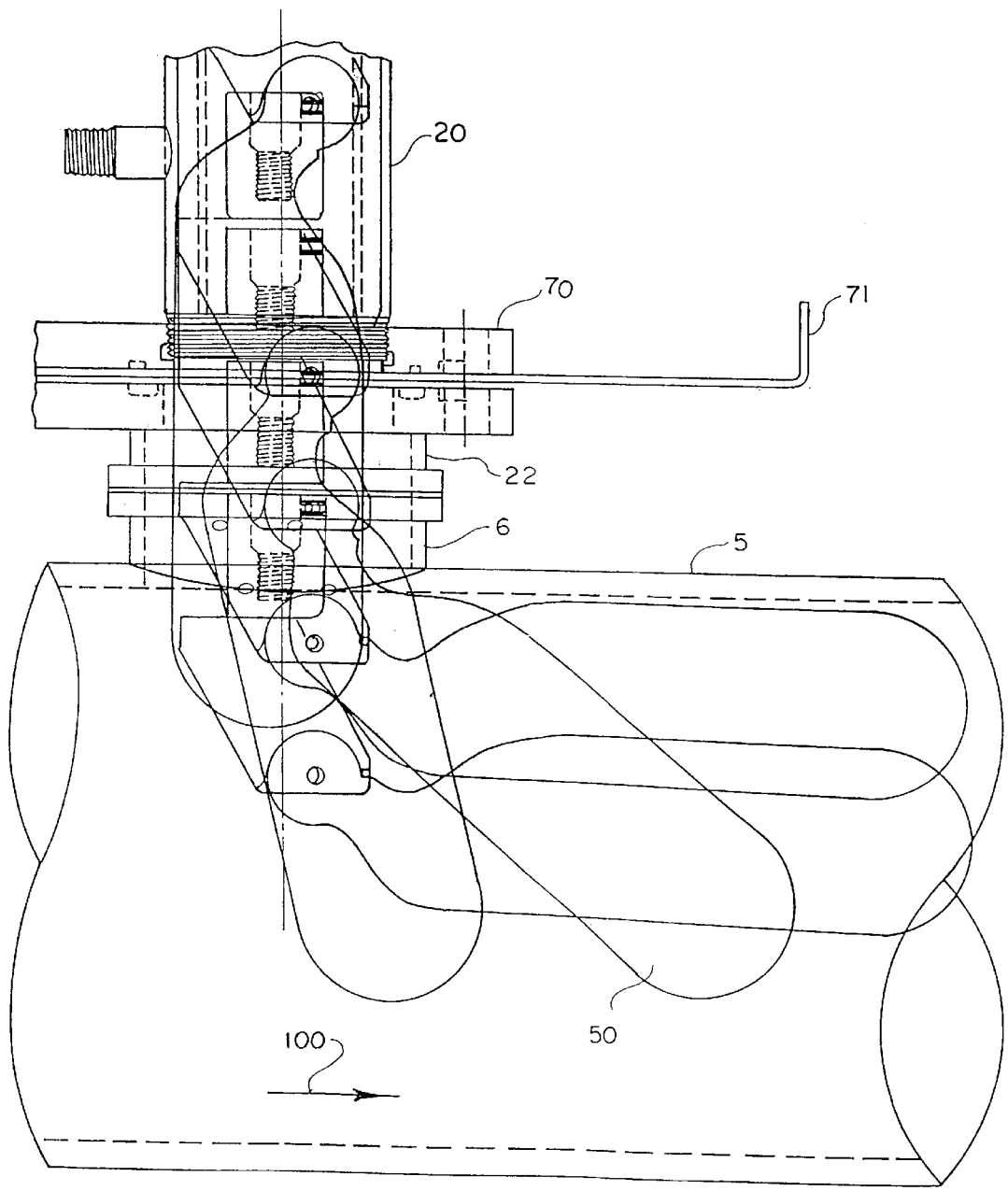
F I G. 1d

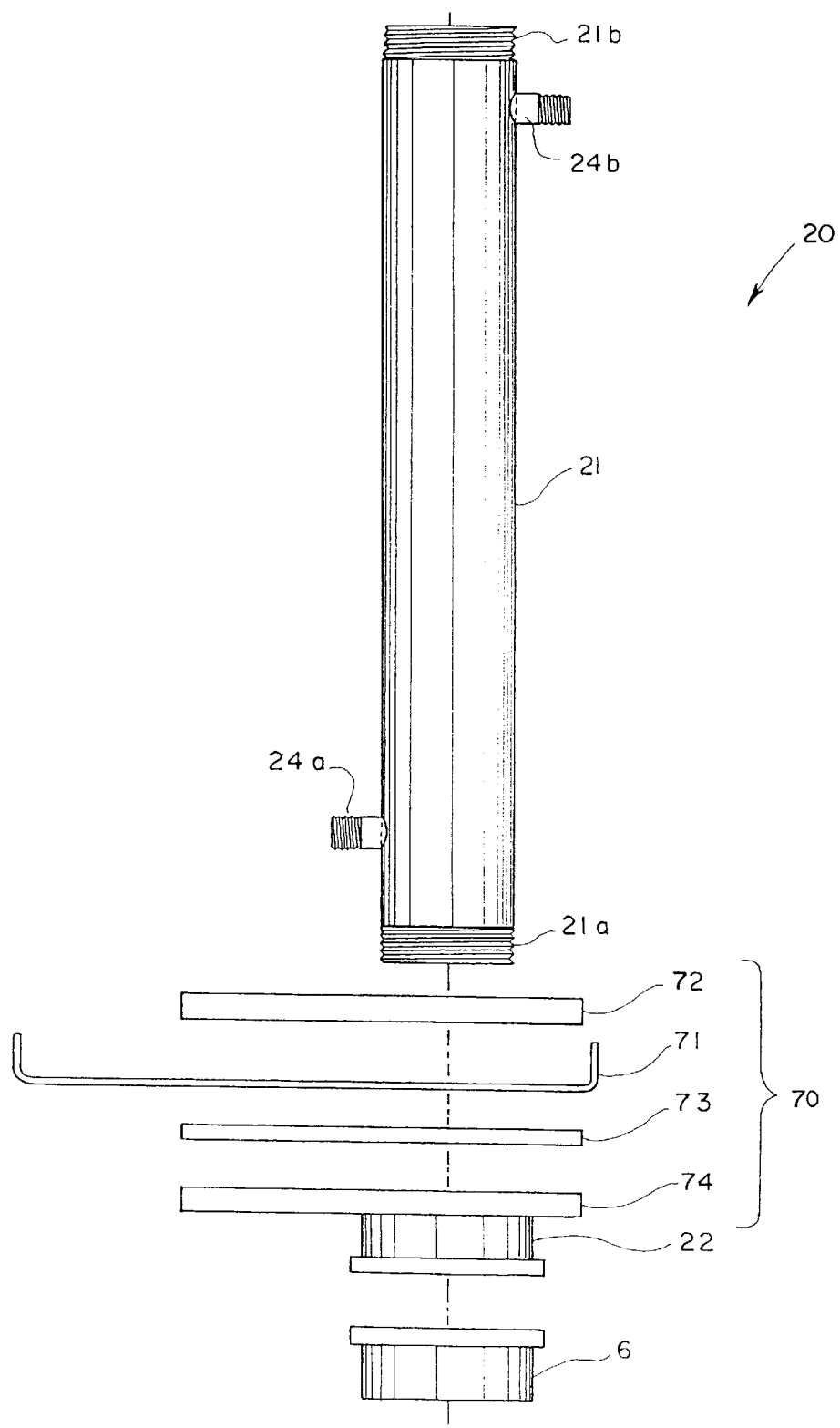
F I G. 2

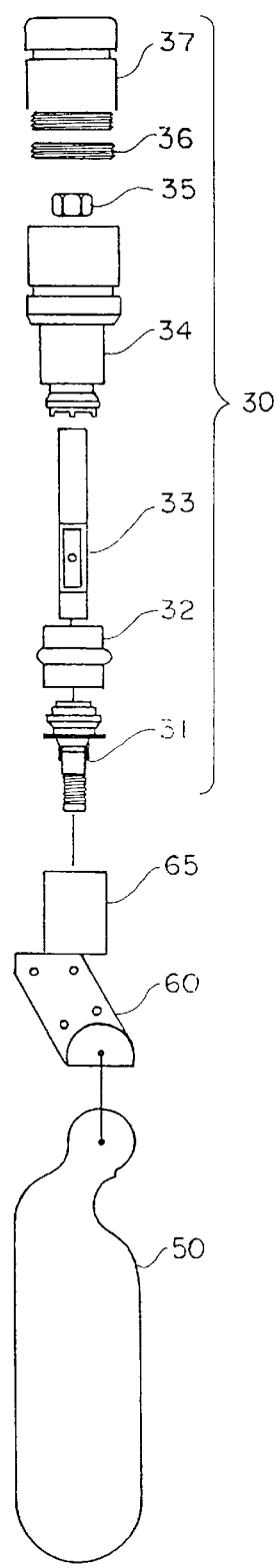
F I G. 3

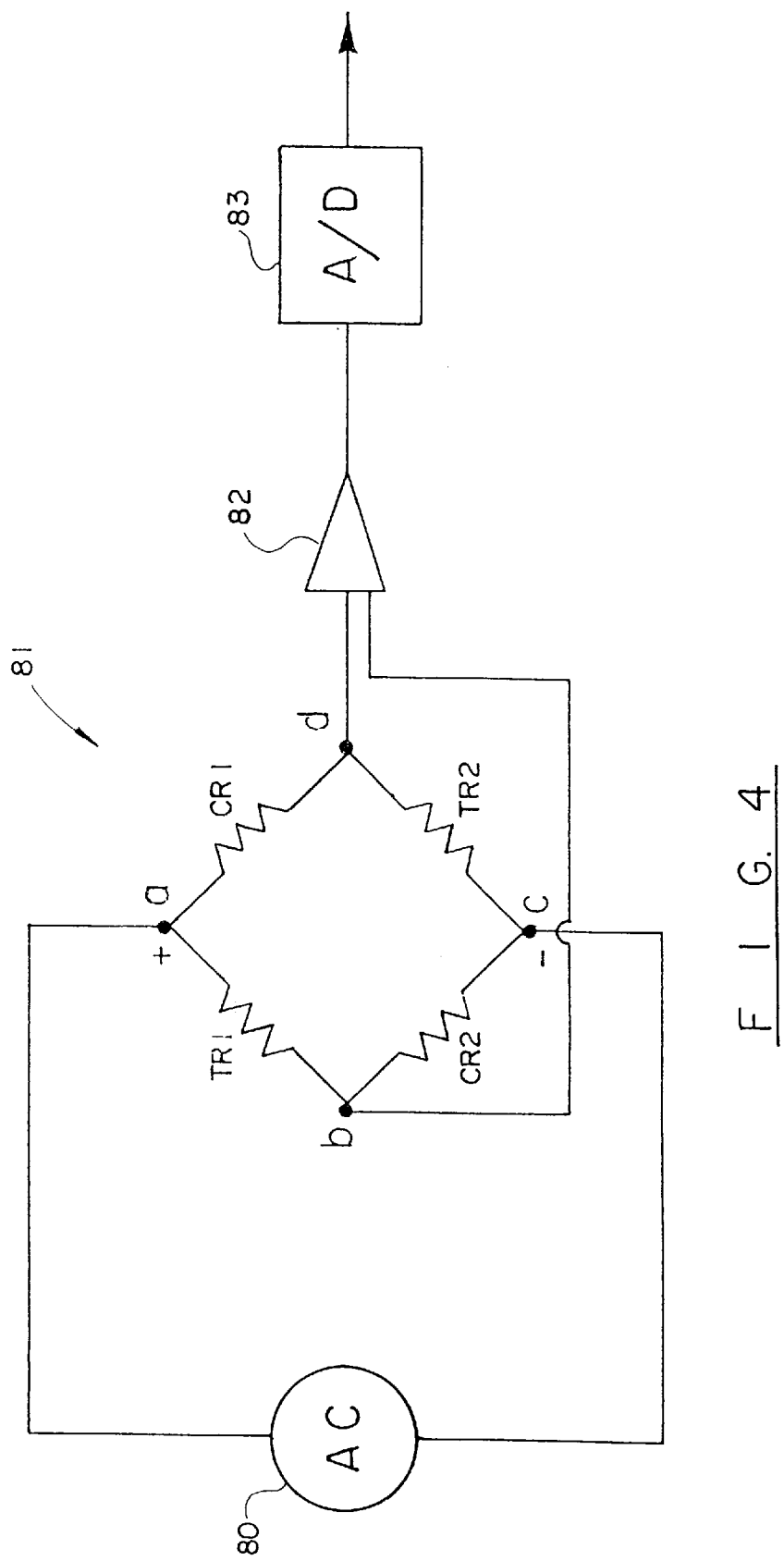
F I G. 4

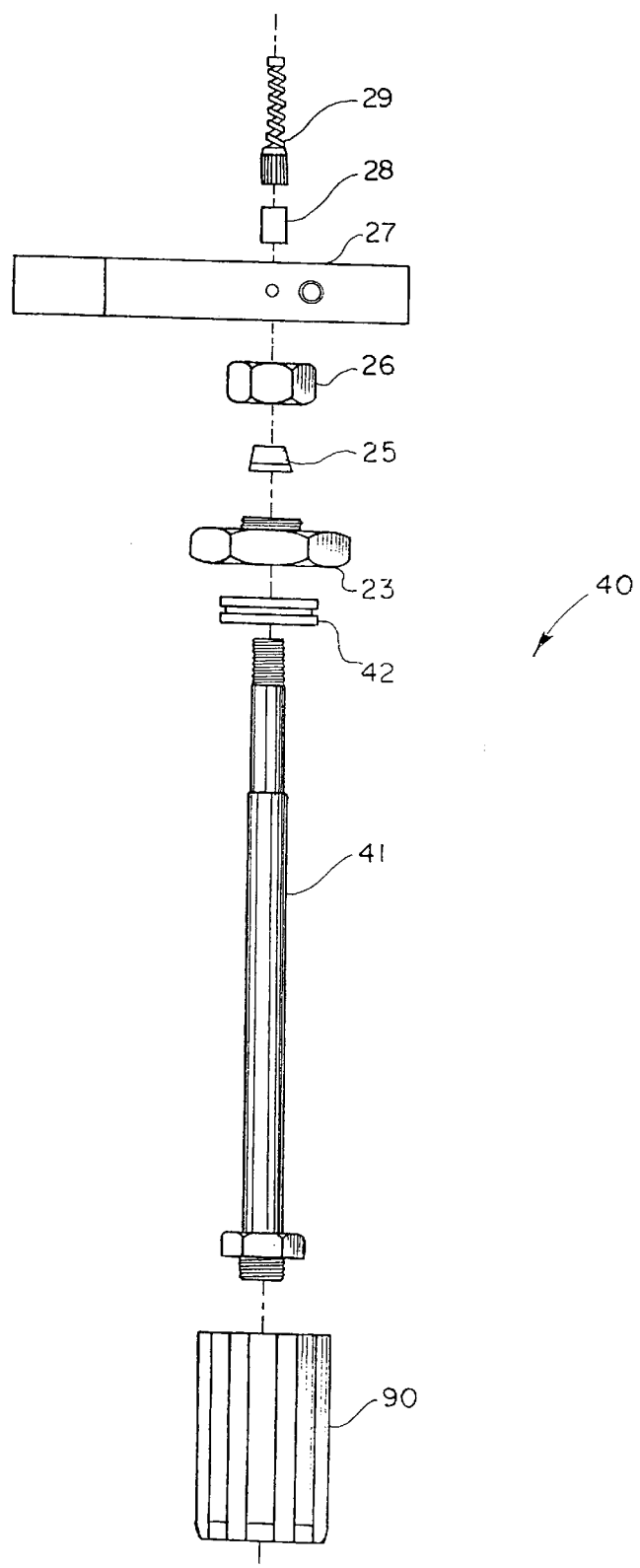
F I G. 6

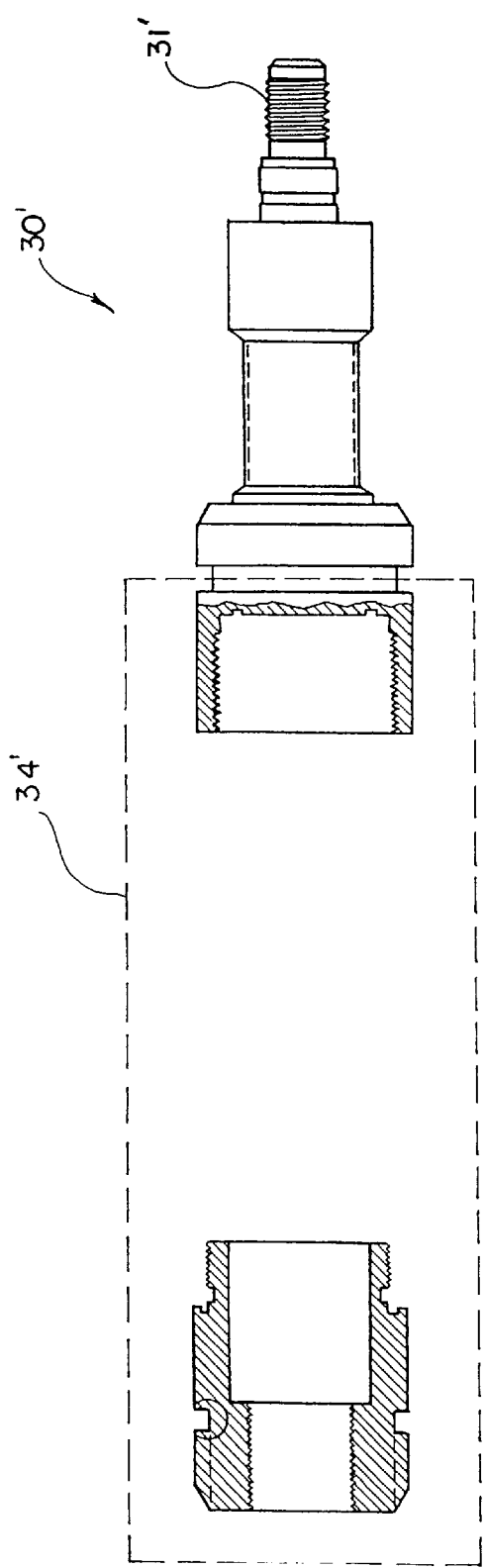

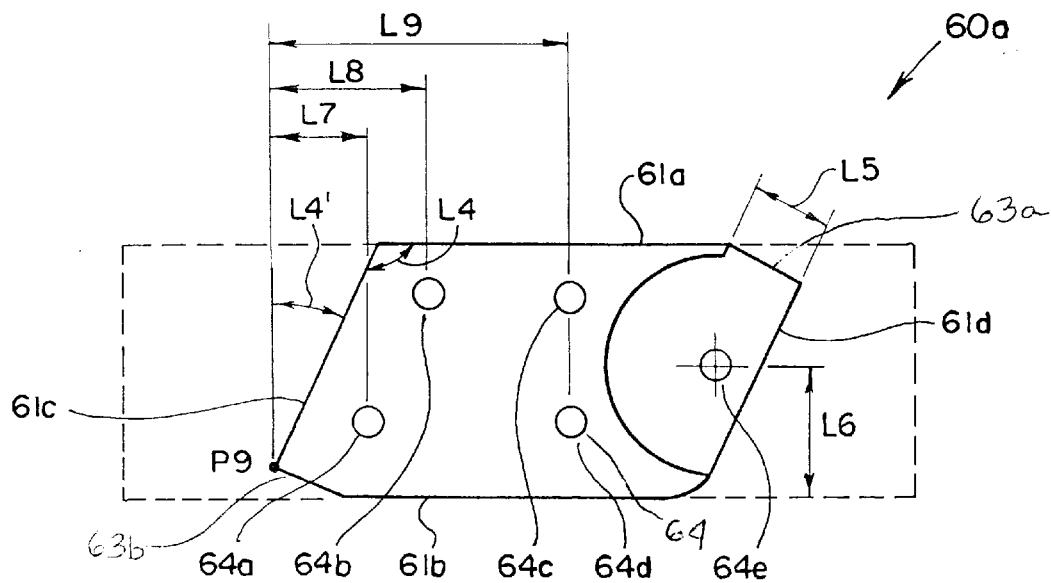
F I G. 9a
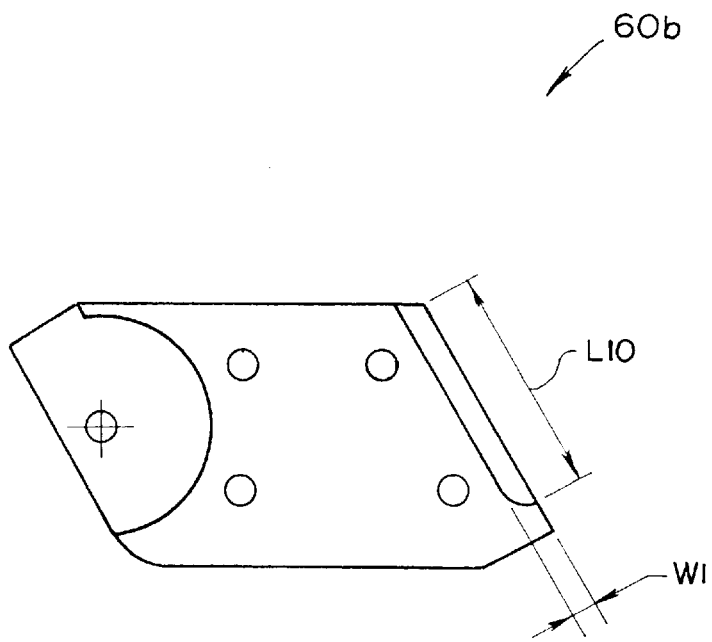
F I G. 9b

SERVICEABLE MEASURING DEVICE

This application is a continuation of Ser. No. 08/808,210 filed Feb. 28, 1997, now U.S. Pat. No. 5,844,152.

TECHNICAL FIELD

The present invention relates to measuring devices utilizing in-line transducers for measuring the apparent viscosity or consistency of particles suspended in a medium and, in the preferred embodiment, to a measuring device which maximizes the surface area of a blade transducer, which is swingably coupled to a probe member, and utilizes the force of the medium, such as a slurry, flowing in an in-service pipeline to swingably align the blade transducer in a desired measuring position. The swingable coupling of the blade transducer to the probe member provides for the retraction from and insertion into the medium flowing in the in-service pipeline for repairs, replacement, or sanitization or other maintenance or servicing of such blade transducer, without shutting down the pipeline and related processes, without compromising the integrity of or disturbing the connection (sealed, flanged, welded or otherwise) between the measuring device and the transducer port in such pipeline and significantly minimizing the environmental exposure of the medium. Moreover, the retractability feature of the swingable blade transducer enables other components of the measuring device to be replaced, repaired and sanitized or otherwise maintained or serviced, as desired.

BACKGROUND OF THE INVENTION

Many consistency or viscosity measuring devices submerge blade transducers, coupled to a shaft-like probe member, into a medium flowing in a pipeline, such as described in U.S. Pat. No. 3,796,088, by Gustafsson et al.; U.S. Pat. No. 4,062,226, by Hietala; U.S. Pat. No. 4,148, 215, by Hofstetter, Jr.; U.S. Pat. No. 4,365,519, by Hietaranta; U.S. Pat. No. 4,677,846, by Lundberg; U.S. Pat. No. 4,757,708, by Hietaranta; and U.S. Pat. No. 5,369,987, by Nettamo et al. Such devices measure various parameters of a medium flowing in a pipeline, such as the viscosity of a liquid, the concentration of solid matter in a liquid, consistency of flowing pulp stock or paper stock fibre, etc.

As can be readily viewed from the above identified patents, the length of the blade transducers extend in the direction of the flow of the medium under test wherein the forces of the medium that are acting upon the blade transducers and probe members are measured to determine the desired parameter of the medium. In order to achieve accurate measurements, the total surface area of the blade transducers should be maximized wherein the height and length which are parallel to the flow of the medium are maximized and the width (the cross-section presented or opposing the flow of the medium) is minimized. As can be observed, such length is significantly greater than the inside diameter of the transducer port into the pipeline. Therefore, to install such consistency measuring devices, the blade transducers thereof must be carefully maneuvered in order to be submerged in the pipeline, when such pipeline is out-of-service. Since the known measuring devices are costly to remove in the event of a malfunctioning component, pipeline servicing, erosion of a component or cleaning of components, the known measuring devices do not provide for maintenance and repair of the measuring devices while the pipeline is in service.

Removal of the blade transducer and probe member of the known measuring devices requires the pipeline to be placed out-of-service. Moreover, the known measuring devices are not capable of removing or inserting the blade transducers from the medium without shutting down the pipeline and related processes, without compromising the integrity of or disturbing the connection (sealed, flanged, welded or otherwise) between the measuring device and the transducer port in such pipeline and significantly minimizing the environmental exposure of the medium.

Other patents present in the art are U.S. Pat. No. 3,734, 119, by Nudds; U.S. Pat. No. 4,875,362, by Skallen; U.S. Pat. No. 5,157,962 by Fitzgerald et al.; and, U.S. Pat. No. 5,349,848, by Driver all of which are directed to measuring devices having blade-like transducers submerged in a medium, but do not meet the needs of the measuring device of the present invention.

Depending on the industrial applicability, it is highly desirable to remove from time-to-time the submerged blade transducers from the pipeline, while such pipeline is in service. In the food industry, such as, without limitation, plants which produce tomato juice, orange juice and ketchup, the pipeline and associated equipment need to be sanitized. In order to remove such blade transducers of known measuring devices from the pipeline, the pipeline must be placed out-of-service and the measuring device, as a whole, must be disassembled in order to retract (i.e., remove) the blade transducer. As is evident, this process is time consuming and costly.

In the paper industry, some of the chemicals used in the process of making paper can corrode the sensing means of the probe members and erode the surfaces of such blade transducers and probe members. Therefore, the blade transducers and sensing means must be repeatedly monitored and replaced. Again, in order to retract the blade transducers of known measuring devices, the pipeline must be placed out-of-service and the measuring devices, as a whole, must be disassembled in order to retract (i.e., remove) the blade transducers of known measuring devices. In the event, a log (dried out paper pulp) passes through the pipeline, all the blade transducers in the pipeline will be damaged and/or dislodged, since such blade transducers cannot be easily and quickly retracted (i.e., removed) from the pipeline. The dislodged blade transducers flow down the pipeline and into the processing equipment which can cause damage to such equipment.

In other materials application, as well as the above mentioned applications, build-up of material on the blade transducer and sensing means are common and such build-up can render the measurements less effective. Therefore, it is highly desirable to retract the blade transducers from the pipeline for cleaning.

It can be readily seen that there exists the continuing need for a measuring device which maximizes the surface area of a blade transducer, which is swingably coupled to a probe member, and utilizes the force of the medium, such as a slurry, flowing in an in-service pipeline to swingably align the blade transducer in a desired measuring position and wherein the swingable coupling of the blade transducer to the probe member provides for the retraction from and insertion into the medium flowing in the in-service pipeline for repairs, replacement, or sanitization or other maintenance or servicing of such blade transducer, without shutting down the pipeline and related processes, without compromising the integrity of or disturbing the connection (sealed, flanged, welded or otherwise) between the measuring device and the transducer port in such pipeline and significantly minimizing the environmental exposure of the medium.

Moreover, the retractability feature of the swingable blade transducer enables other components of the measuring device to be replaced, repaired and sanitized or otherwise maintained or serviced, as desired

ADDITIONAL BACKGROUND INFORMATION

Consistency Measurement

The term consistency is defined as the mass ratio of solids to total stock expressed as a percentage. A commonly used definition in the paper industry is the mass ratio of fiber to total stock, again expressed as a percentage.

Several devices are used to provide on-line measurement of paper stock consistency. Paper stock consistency is not directly measured, but instead some other parameter is measured and related to consistency. Many types of devices and different technologies have been employed to infer a consistency value from some other pulp mixture measurement.

Mechanical Sensing

Mechanical sensors used to indicate consistency or changes in consistency all measure some form of drag force created by a flowing stock stream. One common means of measuring consistency in a flowing stock line is to measure the drag force exerted on an object in the flowing stock stream. For a given stock velocity (flow rate), the force exerted on the object is larger for a higher consistency due to an increased drag force.

Sources of Drag Force

Fluid Shear

For laminar flow in pipe, the velocity of a Newtonian fluid at the wall of the pipe is zero. A fluid layer slightly away from the pipe wall is moving, and exerts a force on the layer on the wall. This force is transferred to the pipe wall. This same scenario occurs for any flat stationary surface in a pipe. The rate at which two adjacent layers of flow pass each other (dv/dx=S) is called the shear rate. The force per unit area (F/A=F') required to cause the shear rate is called shear stress. Newtonian fluid dynamics considers the relationship of shear rate to shear stress of the form $$F\_=\eta S$$

where $\eta$ is a constant called the coefficient of viscosity. For non-Newtonian fluids, the coefficient of viscosity is not a constant and is referred to as apparent viscosity. A pseudo-plastic is a non-Newtonian fluid where the coefficient of viscosity decreases with increasing shear rate. Paper stock gradually changes characteristics with consistency. It typically acts like Newtonian fluid at lower consistencies (below 0.5%), and as a pseudoplastic at higher consistencies (above 4%).

Fiber Shear

Another force which is applied to a stationary body in a paper stock flow stream is a mechanical force required to untangle or "shear" apart a mass of fiber in a slurry A wood fiber's surface is covered with tiny fibrils or rough curls of the fiber itself. Adjacent fibers tend to mechanically bind themselves together by the gripping and tangling of these fibrils. The more fibers there are in a volume of water, the more likely it is for two or more fibers to find themselves in contact. The greater the number of fibers binding together, the greater the force required to shear them apart. This type of shear force will be referred to as fiber shear force.

Enhancing the Desired Drag Force With Shape

The total shear force exerted on a stationary object in a flowing stream of paper stock includes both fluid and fiber shear. The fluid force and fiber force both act in the same direction but on different surfaces of the object. The fluid force acts primarily on a surface parallel to the flow stream, while the fiber force acts on a blunt surface edge orthogonal to the flow stream. The shape of the object can enhance or attenuate one of the two forces described above depending on the surface area parallel or perpendicular to the flow stream. For instance, consider a cylindrical rod placed in the flow stream with it's longitudinal axis perpendicular to the direction of flow. The round bluff body in the stock stream would have most of the flow force exerted on the profile facing the flow. If the velocity is not excessive, the force is due mostly to the shearing of paper fibers from each other. Very little of this force is due to the fluid induced shear because there is not much surface area for a stationary fluid layer to bind with. A flat blade inserted in the stock line develops little force due to fiber shear, because it has a small profile perpendicular to the flow stream. If the flat blade has a large parallel surface area compared to the perpendicular profile area, most of the force is induced from fluid force. Both types of objects have been used for consistency measurement and each has it's own advantages, depending on the type of stock and sensor installation.

Shaping to the Application

Signal to Noise Ratio

In any measuring device which attempts to infer its measurement from another measurement, it is best to maximize the signal change due to variation in the parameter to be measured and minimize the signal change due to all other variations. In this way, the signal to noise ratio is maximized. Depending on the installation parameters and the type of stock to be measured, a device which measures fluid force sometimes has a better signal to noise ratio than a device which measures fiber force, and vice-versa. Other parameters (noises) which influence forces on a body in a flowing stock stream include, fluid velocity, temperature, fiber length, fibrillation, and pH. In order for a measuring device to be of any use, it must have sufficient signal to noise ratio.

Velocity Induced Noise

Another force exists on the body in a flowing stream which is purely velocity induced. Consider the two surface areas of a stationary body orthogonal to the uninterrupted fluid flow. I call the surface area facing the stream the front profile, and the surface facing away from the stream the rear profile. As the fluid is forced around the front profile, the fluid pressure is increased while it is decreased along it's back profile. This differential pressure exerts a force on the object in the direction of the uninterrupted fluid flow. While some of this force can be offset by wake turbulence vortices on the back surface, the force is still proportional to the square of the velocity. As the velocity gets high this force gets very large compared to the shear force because the shear force increases linearly with velocity. The two shear forces show substantial increase with increasing consistency while the differential pressure force does not. Small fluctuations in velocity are unavoidable and cause the signal to noise ratio to rapidly degrade as the average velocity increases. Any device which infers consistency by measuring the force exerted on a stationary body in a flowing stock stream has a practical upper velocity limit for a desired signal to noise ratio. Because the device which primarily measures fluid shear has a smaller profile on which velocity induced differential pressure can act, it has better signal to noise ratio on higher velocity stock flows. At low flows, there may not be enough fluid shear to create sufficient force to measure the desired consistency signal. Typically the stock fiber has sufficient mechanical binding where the fiber shear measuring device works better at very low velocities.

Changes in Mechanical Binding

Fiber length and fibrillation both affect the mechanical binding properties of the wood fibers. A paper stock refiner changes both fiber length and fibrillation. Wood species also naturally have differing degrees of fiber length and fibrillation. In a mill where recycled stock is used, mechanical binding properties tend to vary to a large degree. The amount of mechanical binding available is also a concern with short fibers and high percentage recycle applications. Both the variance and lack of mechanical fiber binding can cause poor signal to noise ratio for the fiber shear type of sensor. In these cases, a blade type of device is usually superior in performance.

Changes in Apparent Viscosity

Temperature and pH usually have a much larger affect on the fluid shear force than on the fiber shear force. In areas where the amount of bleaching done on the stock varies, or where a refiner might significantly vary the stock temperature, a fiber shear sensing device would usually offer better performance than that of a fluid shear device.

Usable Range

Both fluid and fiber shear devices have a lower consistency limit for a given signal to noise ratio. If the consistency is too low, the fluid and fiber shear for a given consistency change may not be sufficient. This is true to a greater degree for fiber shear than fluid shear, therefore a fluid shear device usually has a lower operating range of consistency. At high consistencies, the fiber shear device has been shown to have a very good signal to noise ratio, especially when the fiber length is long. Sometimes the fiber shear device works better in the higher consistency ranges.

Serviceability

Historically, the biggest advantage that a fiber shear measuring device has had over a fluid shear measuring device, is that it is readily removed from the stock line through a valve while the line is in service. It is more readily removable because it does not have a large surface area. Fluid shear devices are of little or no use unless they have a large enough surface area for which the fluid shear force can act upon. Retracting the traditional blade type of device through a valve would require an extremely large valve, which makes the installed cost of the system prohibitive. Most fluid shear or blade type sensors are not removable. This means that the unit cannot be serviced while the stock line is still in service. Shutting down a stock line in a running paper mill can be very costly. For this reason there are many fiber shear sensors installed in applications more suited to fluid shear devices. There is a continuing need for a fluid shear device which can be easily serviced.

Thus, an object and advantage of my invention is the removable and serviceable blade design. The blade can be installed through a reasonably small valve, has a low original installation cost, and generally maintains all of the performance of the larger permanently installed blade types. The device is based on a hinged or flexible portion of the blade which while being inserted through a valve into the flowing stream, is forced, either by the flow stream or some other means, to a position in which it offers a large flat surface for the application of fluid shear force. When retraction is desired, the blade is pulled and the insertion hole edge pushes the hinge point into the opened position, so that the unit can fit through the small valve opening. Once through, the valve can be closed isolating the extraction chamber from the pipeline. The chamber can then be vented to atmosphere, disassembled, and all parts of the sensor can be replaced or serviced.

U.S. Pat. No. 3,364,730, by Wall is incorporated herein by reference as if set forth below in full.

SUMMARY OF THE INVENTION

The preferred embodiment of the measuring device of the present invention solves the aforementioned problems in a straight forward and simple manner. What is provided is, in the preferred embodiment, a measuring device which maximizes the surface area of a blade transducer, which is swingably coupled to a probe member, and utilizes the force of the medium, such as a slurry, flowing in an in-service pipeline to swingably align the blade transducer in a desired measuring position. The swingable coupling of the blade transducer to the probe member provides for the retraction from and insertion into the medium flowing in the in-service pipeline for repairs, replacement, or sanitization or other maintenance or servicing of such blade transducer, without shutting down the pipeline and related processes, without compromising the integrity of or disturbing the connection (sealed, flanged, welded or otherwise) between the measuring device and the transducer port in such pipeline and significantly minimizing the environmental exposure of the medium. Moreover, the retractability feature of the swingable blade transducer enables other components of the measuring device to be replaced, repaired and sanitized or otherwise maintained or serviced, as desired.

In view of the above, an object of the invention is to provide a measuring device for measuring the apparent viscosity or consistency of particles suspended in a medium wherein the apparent viscosity measures the combined effect of both the fluid shear and fiber shear components of the medium.

Another object of the invention is to provide a measuring device having a swingable blade transducer with a maximized surface area wherein the size of the surface area is proportional to the accuracy of the measurement. More specifically, the larger the surface area, the better the signal-to-noise ratio which can be achieved.

A further object of the invention is to provide a measuring device having a swingable blade transducer which has a maximized surface area in relation to the inside diameter of a transducer port and the inside diameter of a pipeline wherein a first dimension of the blade transducer is slightly less than the inside diameter of said transducer port and a second dimension of the blade is maximized to the inside diameter of the pipeline. The first dimension of the blade transducer is parallel to said medium when the blade transducer is retracted from the medium, in a retracted state, and the second dimension of the blade transducer is substantially parallel to said medium when the blade transducer is inserted in the medium, in an insertion state, and aligned in its measuring position. The overall configuration of the blade transducer is optimized to provide a smooth transition from the retracted state to the insertion state.

It is a still further object of the invention to provide a measuring device having a swingable blade transducer which has a length greater than the inside diameter of the transducer port of a pipeline.

It is a still further object of the invention to provide a measuring device having a swingable blade transducer which is aligned in the flow of the medium by the forces acting thereupon.

It is a still further object of the invention to provide a measuring device comprising a swingable blade transducer and suspended probe member having a sensor means which can be retracted from the pipeline while the pipeline is in-service.

It is a still further object of the invention to provide a measuring device comprising a swingable blade transducer and a suspended probe member having a sensor means wherein the blade transducer and suspended probe member may be retracted from the pipeline without compromising the integrity of a seal between an retraction chamber and the transducer port of the pipeline.

It is a still further object of the invention to provide a valve member which isolates the pipeline from a chamber of said measuring device having retracted therein the swingable blade transducer such that the medium flowing in the pipeline is not exposed to the environment.

It is a still further object of the invention to provide a blade measuring device for measuring fluid shear force which can be repeatedly inserted and retracted from an in service pipeline through an isolation valve wherein the cross-sectional area of the blade is significantly greater than the cross-sectional area of the valve aperture.

It is a still further object of the invention to provide a measuring device having a swingable blade transducer and a suspended probe member having a sensor means which can be retracted from time-to-time for cleaning, replacement, and repair.

In view of the above objects, a feature of the present invention is to provide a measuring device comprising a swingable blade transducer and a suspended probe member having a sensor means which can be quickly and easily retracted from and inserted into a medium flowing in a pipeline.

Another feature of the present invention is to provide a measuring device which is simple to use and inexpensive to manufacture.

A further feature of the present invention is to provide a swingable blade transducer and suspended probe member comprising a sensor means which are easily replaced and repaired.

The forgoing and other objects and features of the present invention will become apparent from the drawings, the description given herein, and the appended claims.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein:

FIG. 1d illustrates a plurality of intermediary states between the retraction state and the insertion state of the present invention;

FIG. 2 illustrates a detailed exploded view of the retraction chamber, valve member, transducer port connection member and transducer port coupled theretogether of the preferred embodiment of the present invention;

FIG. 3 illustrates a detailed exploded view of the probe member, probe attachment member, oblique arm and swingable blade transducer of the preferred embodiment of the present;

FIG. 4 illustrates a schematic diagram of the strain gauge of the preferred embodiment of the present invention;

FIG. 5b illustrates a view of the overall configuration of the swingable blade transducer of the embodiment of FIG. 5a;

FIG. 5c illustrates a partial view of the overall configuration of the swingable blade transducer of the embodiment of FIG. 5a;

FIG. 6 illustrates an exploded view of the suspension spindle, retraction/insertion shaft member 40, and seal cap of the present invention;

FIG. 7a illustrates an alternative embodiment of the probe member of the present invention;

FIG. 7b illustrates a portion of the probe top of an alternative embodiment of the probe member of the present invention;

FIG. 8c illustrates an cross-sectional view along the plane 1—1 of FIG. 8a;

FIG. 9a illustrates a view of the male half of the oblique arm of the present invention; and FIG. 9b illustrates a view of the female half of the oblique arm of the present invention;

DESCRIPTION OF THE EXEMPLARY EMBODIMENT

Figure 1A:
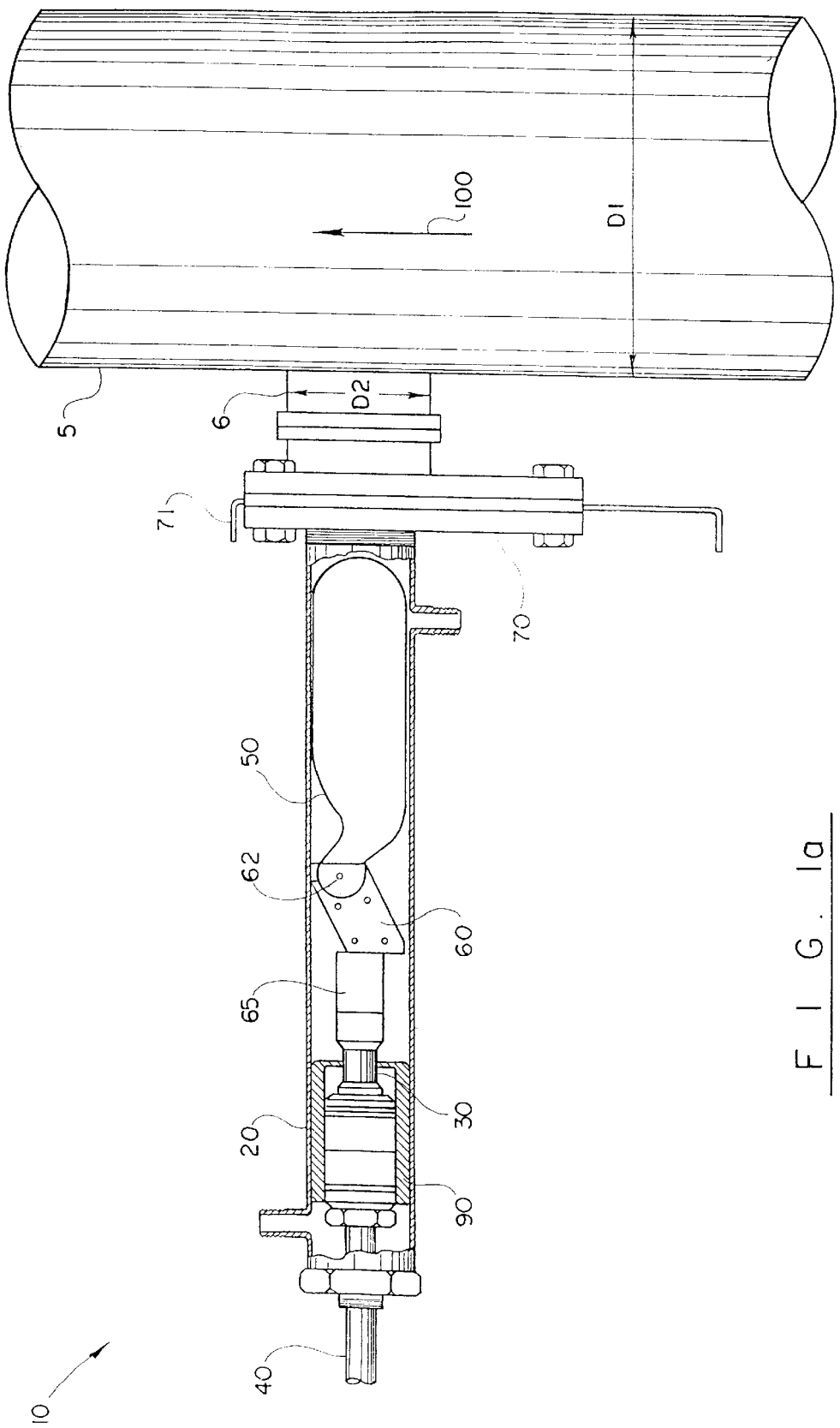
FIG. 1a illustrates the preferred embodiment of the measuring device in the retraction state of the present invention.
Figure 1B:
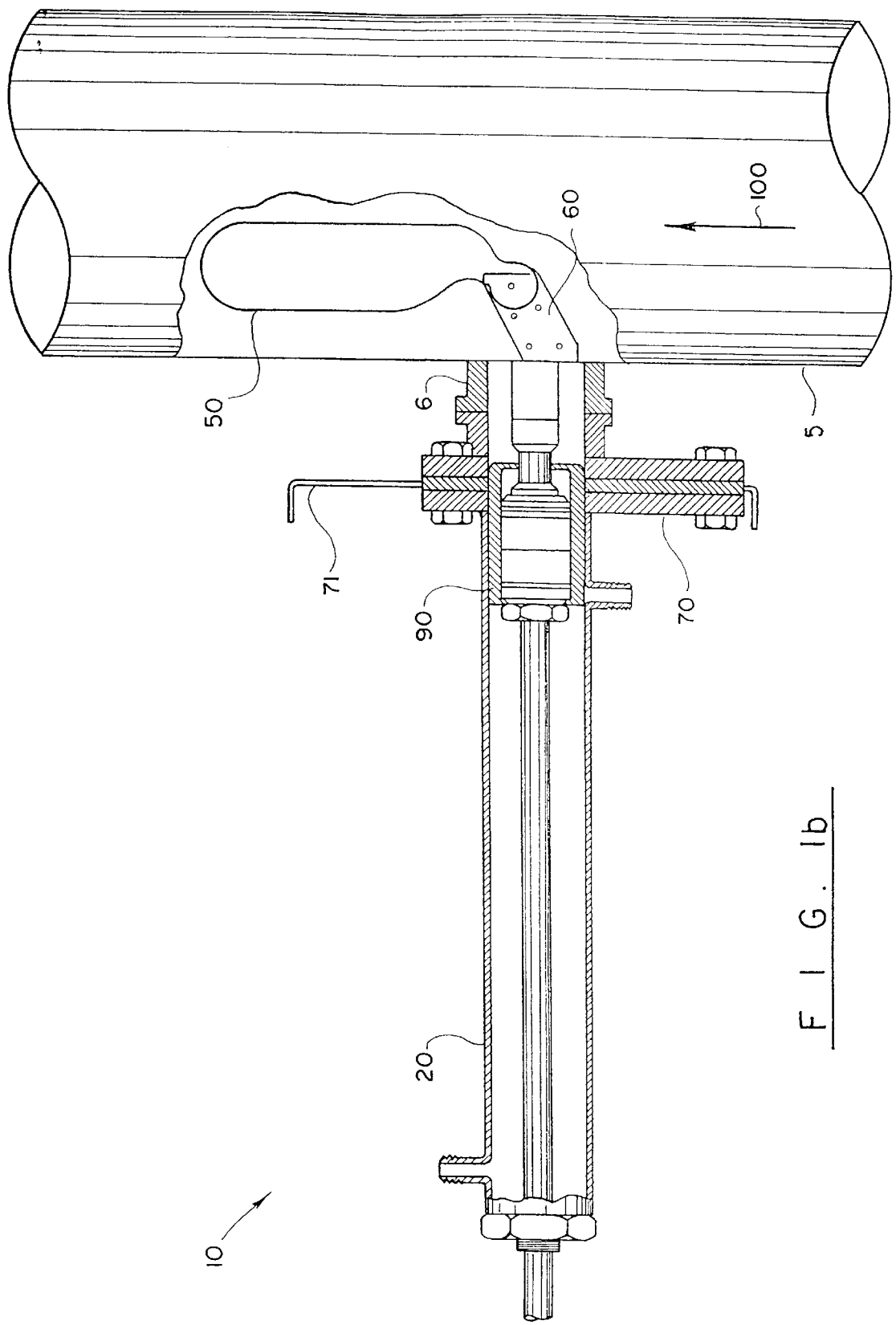
FIG. 1b illustrates the preferred embodiment of the measuring device in the insertion state of the present invention.

Referring now to the drawings, and in particular FIGS. 1a and 1b, the measuring device of the present invention is designated generally by the numeral 10. Measuring device 10 is adapted to be coupled to pipeline 5 having flowing therein a medium, such as a slurry. Pipeline 5 has a predetermined inside diameter D1 and has transducer port 6 coupled thereto with an inside diameter D2. A transducer port with a 2¼ inch inside diameter is commonly found in pipelines in the pulp and paper industry. Nevertheless inside diameter D2 of a transducer port may vary from pipeline-to-pipeline and industry-to-industry.

Measuring device 10 is comprised of retraction chamber 20, probe member 30, retraction-insertion shaft member 40, swingable blade transducer 50, oblique arm 60, probe attachment member 65, pivot means 62, valve member 70 and transducer port connection member 22. FIG. 1a shows measuring device 10 in the retraction state and FIG. 1b shows measuring device 10 in the insertion state.

Referring to FIG. 2, retraction chamber 20 comprises chamber member 21, a hollow cylinder. The inside diameter of said hollow cylinder is substantially equal to inside diameter D2 of transducer port 6 in the preferred embodiment. Nevertheless, the inside diameter of transducer port 6 may be larger than said inside diameter of said hollow cylinder. If transducer port 6 is smaller than the inside diameter of said hollow cylinder, swingable blade transducer 50 may be obstructed from passing through transducer port 6. The length of said hollow cylinder is sufficient to house at least the length of probe member 30, the length of suspension spindle 90, the length of swingable blade transducer 50, the length of oblique arm 60, and probe attachment member 65 such that when swingable blade transducer 50 is fully retracted in retraction chamber 20, which corresponds to the retraction state, as best seen in FIG. 1a, the valve member 70 maybe positioned in the closed state.

In the preferred embodiment, in close proximity to transducer connection member 22, retraction chamber 20 has coupled thereto valve member 70 for opening and closing retraction chamber 20 from pipeline 5 wherein pipeline 5 can be isolated from retraction chamber 20 after swingable blade transducer 50 is retracted beyond valve gate door 71 of valve member 70. Henceforth, the environmental exposure of the medium flowing in pipeline 5 is significantly minimized thereby the integrity of the medium is not compromised and the pipeline and related processes can continue to operate when measuring device 10 is in the retraction state.

Valve member 70 comprises valve gate door 71, first flange 72, spacer 73 and second flange 74 wherein valve gate door 71, first flange 72, spacer 73 and second flange 74 each have formed therein an aperture having a inside diameter at least the size of said inside diameter of retraction chamber 20 for providing a clear unobstructed path to pipeline 5 when valve gate door 71 is in an open position. First flange 72, valve gate door 71, spacer 73, and second flange 74 are sandwiched together such that valve gate door 71 may be slidably moved from a close position to said open position. In said closed position, valve member 70 isolates retraction chamber 20 from pipeline 5. In said open position, valve member 70 allows swingable blade transducer 50 to be inserted into pipeline 5. Chamber member 21 has end 21a thereof threaded for screwably coupling to first flange 72 wherein chamber member 21 may be easily removed therefrom, as desired, while maintaining the medium flowing in pipeline 5 isolated from the environment by valve member 70. Transducer port connection member 22 has one end fixedly coupled to second flange 74 and the other end is coupled to transducer port 6.

While the preferred embodiment provides for valve member 70 coupled to retraction chamber 20, alternatively, valve member 70 may be strategically coupled to or incorporated in transducer port 6. In the preferred embodiment, valve member 70 is a gate valve wherein the use of a gate valve does not significantly increase the overall length from pipeline 5 to the end of retraction chamber 20.

End 21b of chamber member 21 is also threaded for coupling thereto seal cap member 23 for sealing retraction chamber 20 from the environment during the measuring process. Chamber member 21 further comprises first outlet port 24a and second outlet port 24b coupled in close proximity to ends 21a and 21b, respectively, of chamber member 21. First and second outlet ports 24a and 24b each have coupled thereto a relief valve (not shown) for relieving any pressure build-up in retraction chamber 20.

Referring now to FIG. 3, probe member 30 contains means for detecting the drag forces applied to swingable blade transducer 50. Such forces may consist of a moment force created by swingable blade transducer 50 being forced against the stop protrusion 53 thus creating a force which tends to bend a spring element mounted in probe member 30 such that a part of the spring element is placed in tension and a part of the spring element is placed in compression. Other detecting or sensing means may be mounted in or comprise probe member 30 depending on the desired sensing or measuring requirements.

Referring now to FIGS. 7a and 7b, in one version of the preferred embodiment, probe member 30 is a strain gauge assembly comprised of blade attachment member 31, bellows 32, spring element 33, guard element 34, nut 35, lock ring 36 and probe top 37. A first distal end of blade attachment member 31 couples suspended probe member 30 to swingable blade transducer 50 via probe attachment member 65; and, in the preferred embodiment, for purpose of easy maintenance, is threadedly coupled. A second distal end of blade attachment member 31 couples to spring element 33 on which are mounted strain gauges for measuring the flex or strain of such spring element. Spring element 33 comprise a threaded rod with a diameter sized to produce the desired strain or flexing, with back-to-back portions of such threaded rod filed to a flat surface for mounting thereon strain gauge elements. Bellows 32 radially surrounds spring element 33 in order to shield the spring element and, in particular, the strain gauges; and, said bellows 32 is anchored at one distal end by blade attachment member 31 and at the other distal end by guard element 34. Spring element 33 is journaled through guard element 34 and fixed by nut 35; and probe member 30 is finally assembled with lock ring 36 and probe top 37, as known.

An alternative probe member 30' could also be used in the preferred embodiment wherein a collar or short hollow cylinder serves as the spring element and wherein the strain gauges are mounted on the inside surface of said collar or short hollow cylinder. Blade attachment member 31' and spring top 34' are adapted to receive and hold said collar or short hollow cylinder. Spring top 34' is comprised of a union, one end of which is adapted for coupling to said shaft member 41.

Referring now to FIG. 4, the schematic diagram of a strain gauge of the preferred embodiment is illustrated. Said strain gauge comprises AC source 80, wheatstone bridge 81, differential OP-AMP 82, analog-to-digital converter (A/D) 83. The positive side and negative side of AC source 80 are coupled to Terminal a and Terminal c, respectively, of wheatstone bridge 81. Terminals b and d are coupled to the input side of differential OP-AMP 83 wherein the output of wheatstone bridge 81, with respect to Terminals b and d, is differentiated. The output of differential OP-AMP 83 is coupled to the input of A/D converter 83. The output of A/D converter 83 is coupled to a remote microprocessor (not shown) which receives the digital signals from a plurality measuring devices 10 and processes and interprets such digital signals.

Wheatstone bridge 82 further comprises two tension resistive elements TR1 and TR2 and two compression resistive elements CR1 and CR2. Resistive element TR1 has one terminal coupled to Terminal a and the other terminal coupled to Terminal b. Resistive element TR2 has one terminal coupled to terminal c and the other end coupled to terminal d. Resistive element CR1 has one terminal coupled to terminal a and the other terminal coupled to terminal d. Resistive element CR2 has one terminal coupled to terminal c and the other end coupled to terminal b.

In the exemplary embodiment, the schematic diagram of said strain gauge illustrates one of many possible configurations functioning as a strain gauge sensor. Nevertheless, any conventional force measuring sensor many be substituted. In the preferred embodiment, the apparent viscosity or consistency of particles suspended in a medium is measured wherein the combined effect of both the fluid shear and fiber shear components can be determined. Nevertheless, measuring device 10 can be adapted to measure other parameters of a medium flowing in a pipeline, such as, without limitation, the viscosity of a liquid, the concentration of solid matter in a liquid, and consistency of flowing pulp stock or paper stock fiber.

Figure 1C:
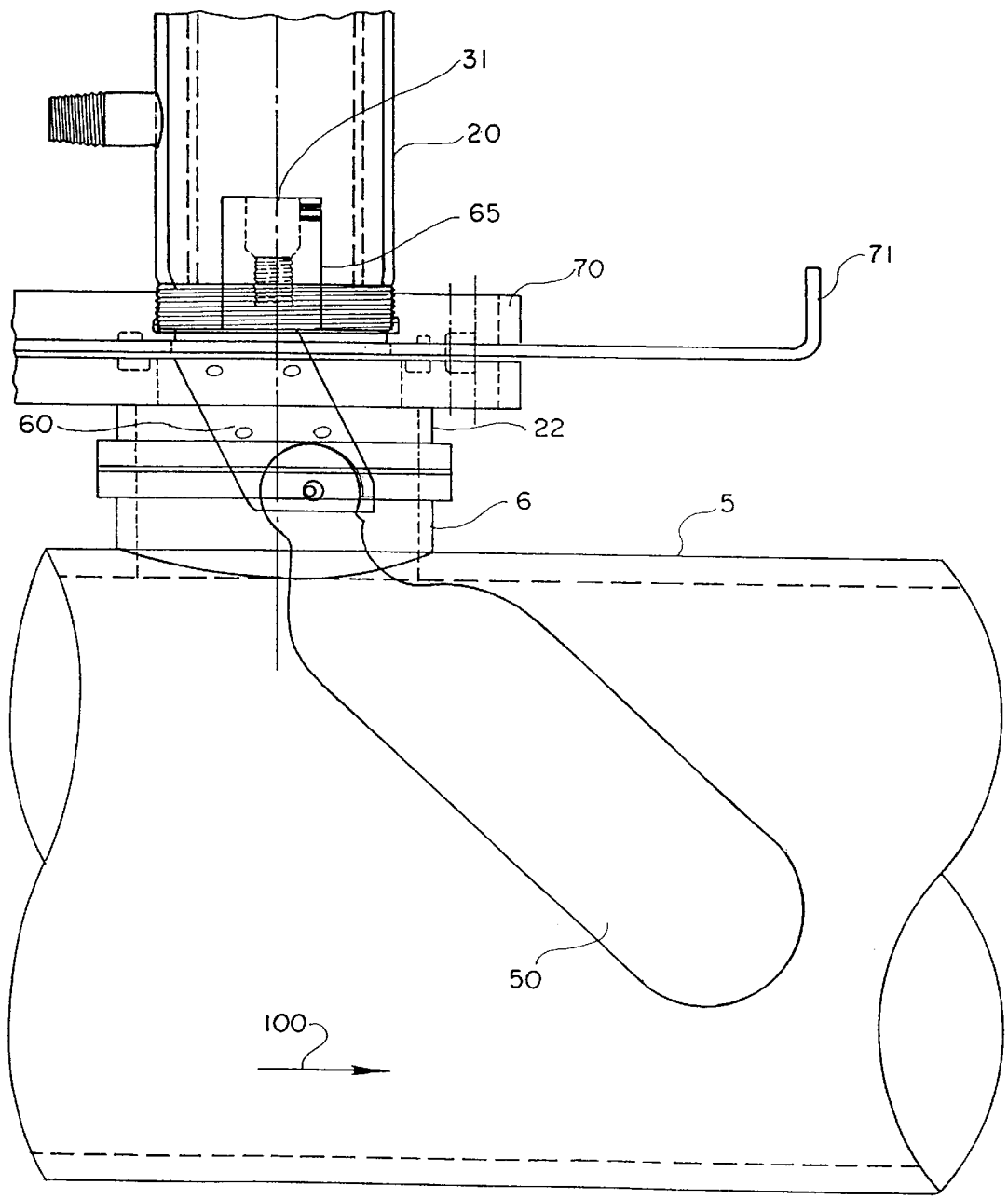
FIG. 1c illustrates an intermediate position of swingable blade transducer as it is being retracted into retraction chamber 20 of the present invention.
Figure 1E:
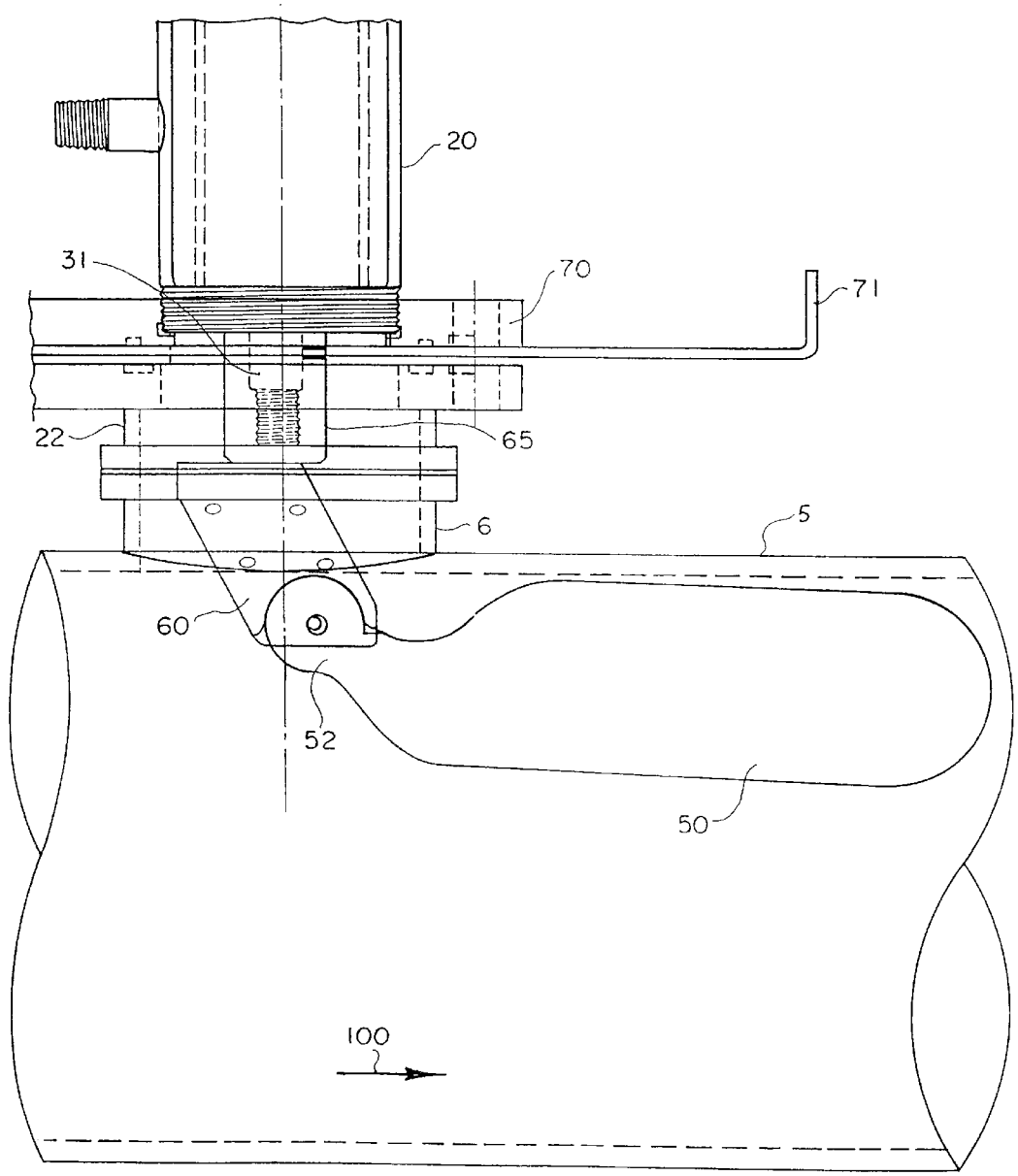
FIG. 1e illustrates a detailed view of the insertion state of swingable blade transducer of the present invention.
Figure 5A:
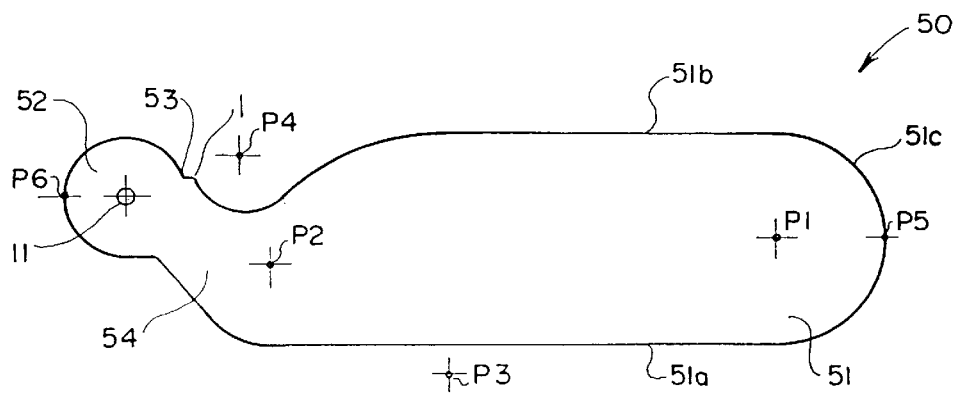
FIG. 5a illustrates a view of the overall configuration of the swingable blade transducer of an exemplary embodiment of the present invention.
Figure 5B:
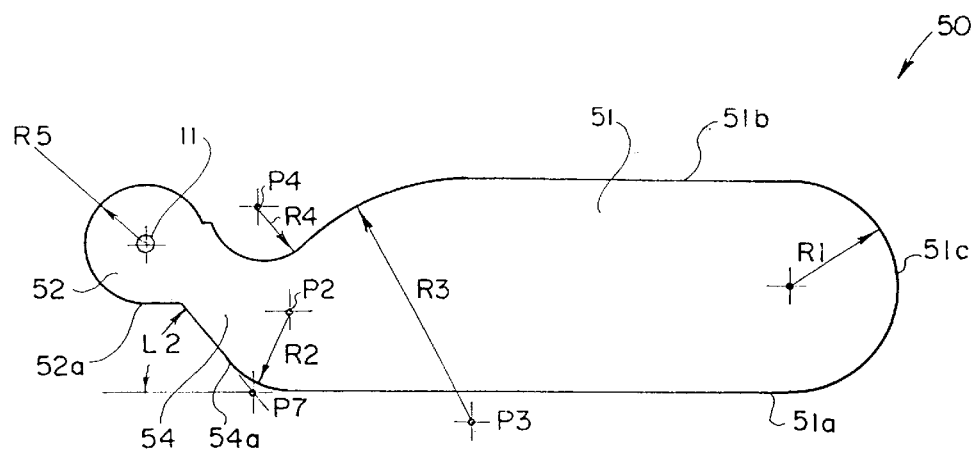
Figure 5C:
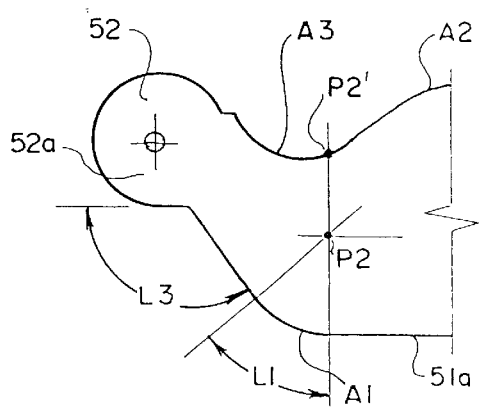

Referring to FIGS. 5a, 5b and 5c, the overall configuration of swingable blade transducer 50 comprises quasi-rectangular shaped structure 51, pivot head 52, stop protrusion 53, hunched angling neck member 54. Swingable blade transducer 50, swingably (i.e., rotatably) couples to one distal end of probe member 30 via blade attachment member 31 coupled to probe attachment member 65 having fixedly coupled thereto oblique arm 60. Swingable blade transducer 50 has a first orientation in a retraction state with respect to said one distal end of probe member 30 and a second orientation, substantially different from said first orientation with respect to said one distal end of probe member 30, in said insertion state wherein swingable blade transducer 50 freely rotates to said second orientation for measuring a parameter of the medium and freely rotates to said first orientation when entering retraction chamber 20, as best seen in FIGS. 1c and 1d.

Quasi-rectangular shaped structure 51 is defined by a rectangular surface area within first and second long sides 51a and 51b and a first short side coupled to hunched angling neck member 54 and a curved end 51c which is rounded or curved on a second short side; and in the preferred embodiment curved end 51c is a semi-circular area. Curved end 51c is defined by radius of R1 with respect to point P1, the mid point between line 51a and 51b, wherein for a given pipeline inside diameter D1, the length of swingable blade transducer 50 may be maximized such that curved end 51c nearest 51a passes slightly above or slidably rolls along the inner surface of pipeline 5 when transitioning between the retraction state and the insertion state.

In a preferred embodiment, hunched angling neck member 54 allows aperture 11 of pivot head 52 to be offset from the center plane defined between line 51a and line 51b. The first short side of first long side 51a merges with arc A1 having a radius R2 with respect to point P2 wherein the arc length of arc A1 is defined by angle L1 with respect to point P2. Arc A1 merges with line 54a of hunched angling neck member 54 wherein the slope of line 54a forms angle L2 with respect to Point P7, the intersection of line 54a and line 51a. Second long side 51b curves to form an arc A2 having a radius R3 with respect to point P3. Arc A2 merges with arc A3 having a radius R4 with respect to point P4 wherein arc A2 and arc A3 intersect at Point P2'. Arc A2 peaks at apex 1 whereby stop protrusion 53 is formed. Stop protrusion 53 is a substantially triangularly shaped projection formed between arc A3 and pivot head 52. The contour defined by arc A2 and arc A3 serves to guide, move and position swingable blade transducer 50 around the juncture defined by transducer port 6 and pipeline 5 so that swingable blade transducer 50 is unobstructed when transitioning from the insertion state to the retraction state, as best seen in FIGS. 1c and 1d. Such contour is selected for the size of transducer port 6 and pipeline 5 and the length of swingable blade transducer 50. The contour of arc A2 and arc A3 is one of many possible configurations capable of serving to guide, move and position swingable blade transducer 50 around the juncture defined by transducer port 6 and pipeline 5 such that swingable blade transducer 50 is unobstructed when transitioning from the insertion state to the retraction.

Pivot head 52 comprises a quasi-circular member having a radius of R5 with respect to the center of aperture 11 formed therein beginning from the base of stop protrusion 53 and ends at line 52a, a substantially flat line. Line 52a merges with line 54a wherein angle L3 is formed.

Stop protrusion 53 engages oblique arm 60 to limit the angle of rotation as swingable blade transducer 50 is aligned in its second orientation by the forces acting thereupon from the flowing medium. The radius of arc A3 allows swingable blade transducer 50 to freely rotate continuously from its first orientation, as best seen in FIG. 1a to its second orientation, as best seen in FIGS. 1c and 1d. More specifically, as a significant portion of swingable blade transducer 50 extends in the flow of said medium, the forces of said medium begin to act thereon. Eventually, swingable blade transducer 50 begins to freely rotate in the direction of the flow of said medium. The curvature of arc A3 eventually conforms to the juncture defined by pipeline 5 and transducer port 6 whereby swingable blade transducer 50 is unhindered in its rotation to its second orientation.

Pivot head 52 of swingable blade transducer 50 pivotally couples to oblique arm 60 via pivot means 62. In the exemplary embodiment, pivot means 62 is a pivot pin fixedly coupled to the interior of oblique arm 60. Nevertheless, pivot head 52 in combination with pivot means 65 may be substituted with any suitable component, such as, without limitation, a hinge, ball joint, which is capable of allowing swingable blade transducer 50 to freely rotate such that swingable blade transducer 50 becomes aligned by the forces acting thereupon.

For exemplary purposes, the inside diameter D2 of transducer port 6 is within the range of 2.25–2.75 inches. R1 is 1 inch; R2 is ¾ of an inch; R3 is 2.25 inches; R4 is ½ of an inch; and, R5 is ½ of an inch. Point P1 is located approximately in the center between lines 51a and 51b wherein the distance between parallel lines 51a and 51b is 2 inches. Point P2 is located approximately ¾ of an inch from line 51a and 1.283 inches from the center of aperture 11. Angle L1 is approximately 50°. Point P3 is located ¼ of an inch below line 51a and 3.989 inches from Point P5, the apex of said semi-circular surface area. Point P2' is substantially equal to 1.283 inches from the center of aperture 11. Angle L2 is approximately 53.146°. Point P4 is located approximately 1.75 inches from line 51a and 5.876 inches from Point P5. The center of aperture 11 is approximately 1.405 inches from line 51a and 1.283 inches from point P2. Apex 1 has a height of 1.582 inches from line 51a. The length of line 54a is 0.816 of an inch. Line 52a has a length of 0.219 of an inch and angle L3 is approximately 122.703° with respect to line 54a. Pivot head P2 begins 0.969 inched from Point P6. The total length of swingable blade transducer 50 is 7.400 inches from Point P5 to Point P6.

While the preferred embodiment of the present invention provides for a blade transducer, in some environments a chain-link-like member or rope-like member (having flexible properties) can be substituted for swingable blade transducer 50 wherein such chain-link-like member or rope-like member may be easily retracted in retraction chamber 20 and valve member 70 closed.

Referring now to

FIGS. 9a and 9b, oblique arm 60 comprises male half 60a and female half 60b wherein male half 60a and female half 60b are coupled in parallel via a plurality of bolting means 64 to form a parallelogram shaped member. In the preferred embodiment, pivot head 52 of swingable blade transducer 50 is sandwiched between male half 60a and female half 60b wherein pivot head 52 pivots therein via pivot means 62 journaled through aperture 11.

Since male half 60a is substantially identical to female half 60b only one such half will be described in detail. The surface area of male half 60a is defined by a first pair of offset parallel sides 61a and 61b and a second pair of offset parallel sides 61c and 61d wherein said first pair and second pair of offset parallel sides are offset by angle L4 wherein L4 is 90 degrees plus L4' which is 26.565 degrees formed by the intersection of side 61a and side 61c. Male half 60a further comprises a pair of truncated opposite corner members 63a and 63b having a length L5 of 0.396 of an inch.

As shown in FIG. 9a, the distance L6 from aperture 64e to line 61b is 0.668 of an inch. The distance L7 from point P9 to aperture 64a is 0.466 of an inch. The distance L8 from point P9 to aperture 64b is 0.770 of an inch. The distance L9 from point P9 to apertures 64c and 64d is 1.489 of an inch.

As shown in FIG. 9b, the length L10 of the portion in female half 60b which has removed material to accommodate a weld bead is 1.079 of an inch. The width W1 of such portion in female half 60b is 0.132 of an inch.

Probe attachment member 65 is a cylindrically shaped member having a hollowed threaded interior for receiving therein blade attachment member 31. Probe attachment member 65 has coupled in the center thereof oblique arm 60. Probe attachment member 65 has a inside diameter D3 which is, in the preferred embodiment, 1 inch. Side 61c of oblique arm 60 is fixedly coupled substantially in the center of probe attachment member 65 wherein side 61c of oblique arm 60 couples 0.725 of an inch thereof in the center of probe attachment member 65 and the remaining portion extends beyond the perimeter of probe attachment member 65.

In the preferred embodiment, the structural arrangement of probe attachment member 65 as coupled to oblique arm 60 is such that when measuring device 10 is in its retraction state, the radial axis of probe member 30 does not intersect pivot means 62 because the pivot means 62 is somewhat offset from such radial axis in order to facilitate the guiding, movement and positioning of the swingable blade transducer 50 as it is pulled into the retraction chamber 20. However, any assembly of parts between the swingable blade transducer and the means for pulling the swingable blade transducer from the pipeline 5 that would serve to align the swingable transducer on its path as it transitions into the retraction chamber 20 would also be within the scope of my invention.

In the preferred embodiment, swingable blade transducer 50, oblique arm 60 and probe attachment member 65 are made of stainless steel.

Retraction-insertion member 40 comprises shaft member 41 and parallel rings 42 which are coupled to one distal end of shaft member 41. Parallel rings 42 are coupled to seal cap 23 wherein as seal cap 23 is opened (and, in the preferred embodiment, unscrewed), shaft member 41 is retracted. As shaft member 41 is retracted, probe member 30 is likewise. Shaft member 41 is hollow for journaling therein electrical wires for connection to said stain gauge.

Referring now to FIG. 6, seal cap 23 is coupled to compression ring 25 and lock nut 26. Strain relief spring member 29 is coupled to end cap 28. Arrow 27 is used to indicate the direction of the flow of the medium.

Figure 8B:
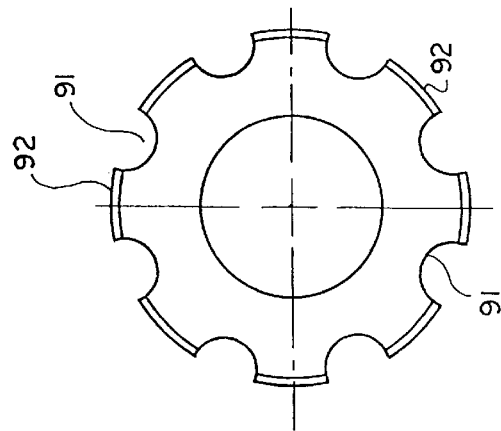
FIG. 8b illustrates an top view of the suspension spindle of the present invention.
Figure 8C:
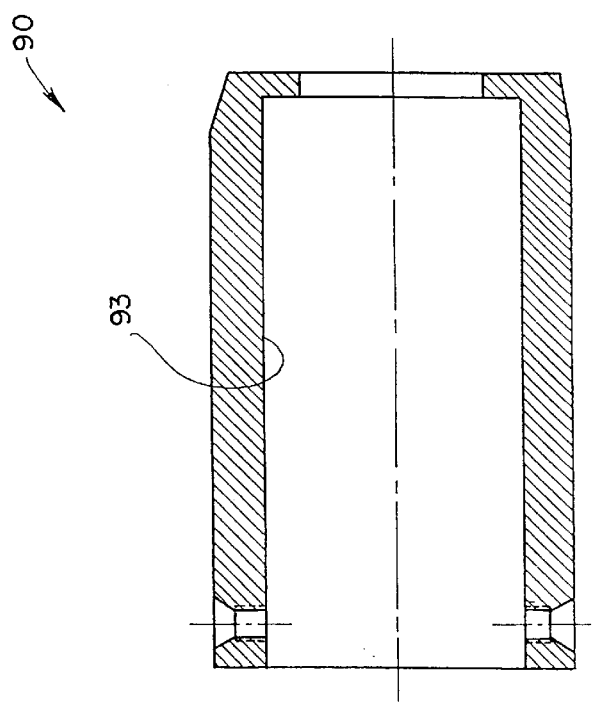
Figure 8A:
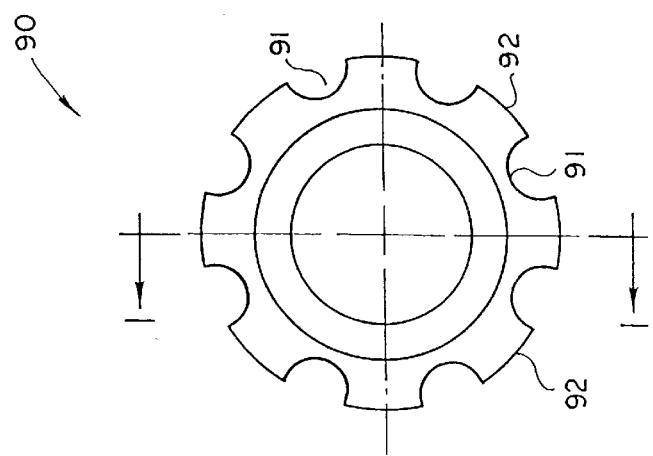
FIG. 8a illustrates an rear view of the suspension spindle of the present invention.

Referring now to FIGS. 8a, 8b, and 8c, in the preferred embodiment, spindle 90 is a hollow cylinder having a plurality of spaced channels 91 formed longitudinally therein. The spaced surfaces 92 between the plurality of spaced channels 91 engage the inner surface of retraction chamber 20. Probe top 37 is received in spindle 90 wherein the outer surface of probe top 37 engages inner surface 93. In the preferred embodiment, spindle 90 is made of TEFLON. Nevertheless, stainless steel, rigid plastic or the like may be substituted. Spindle 90 serves to suspend probe member 30 and retraction-insertion shaft member 40 in the center of retraction chamber 20. In operation, the medium flows through pipeline 5 in the direction of arrow 100, there will be a certain drag force on swingable blade transducer 50, urging swingable blade transducer 50 in the direction of the flow. Swingable blade transducer 50 will exert pressure on probe member 30 which will be detected by said strain gauge.

Figure 10:
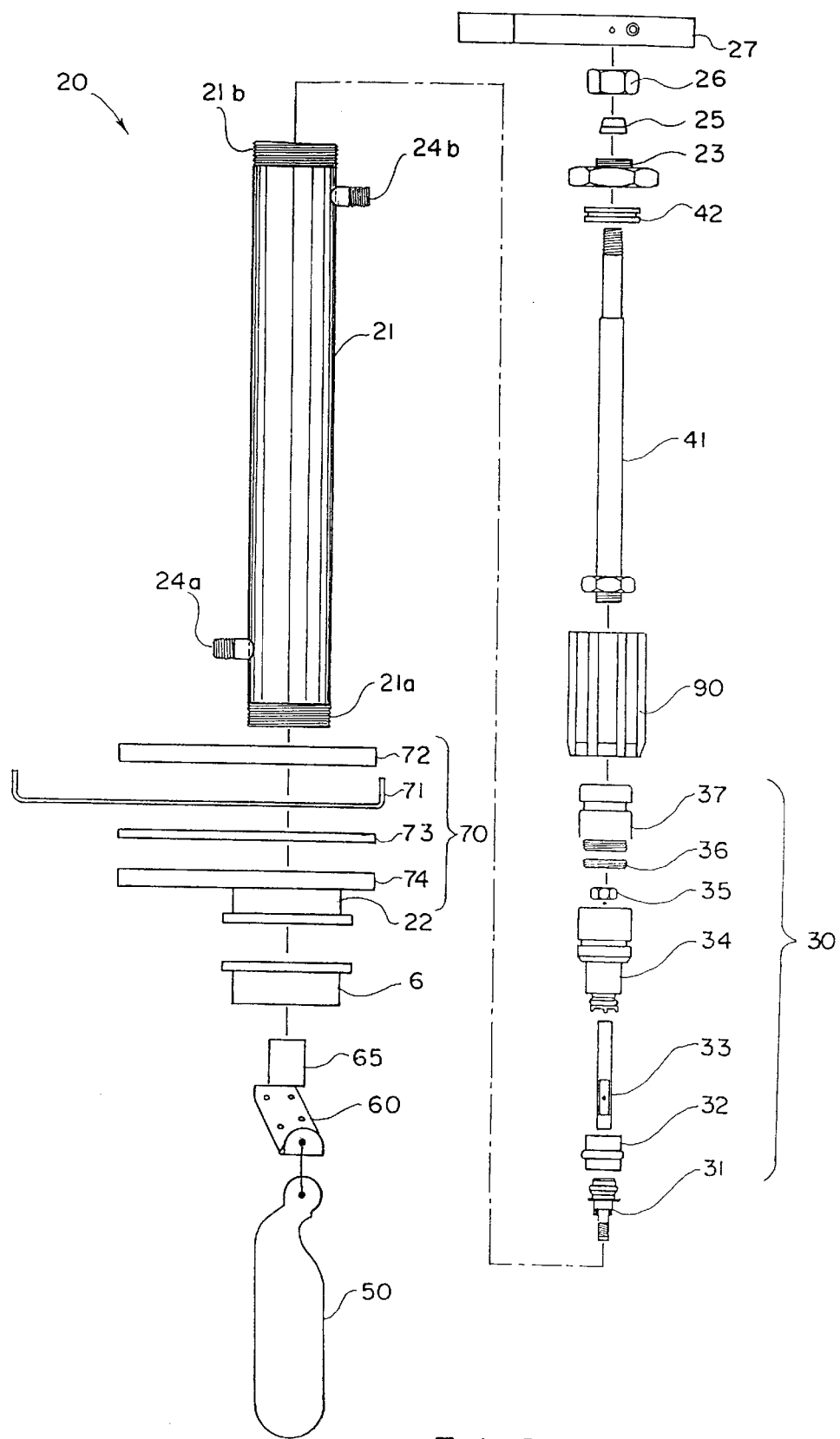
FIG. 10 illustrates a overall exploded view of the measuring device of the present invention.

FIG. 10 illustrates the an exploded of measuring device 10 of the present invention.

In the preferred embodiment of the present invention, measuring device 10 has application in many industries where a medium is flowing in a pipeline. Nevertheless, measuring device 10 comprising retraction chamber 20, probe member 30, retraction-insertion shaft member 40, swingable blade transducer 50, oblique arm 60, probe attachment member 65, pivot means 62, and valve member 70 may be installed in a sea vessel wherein probe member 30 is adapted to measure parameters of a waterway.

It is noted that the embodiment of the measuring device described herein in detail, for exemplary purposes, is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A serviceable measuring device for measuring a parameter of a medium flowing in an in-service pipeline comprising:

a retracting-reinserting shaft with a first end;

a blade transducer having a length dimension and pivotally coupled to said retracting-reinserting shaft at said first end wherein, with respect to said first end, said blade transducer has a measuring orientation for measuring said parameter of said medium and a retracted orientation; and a chamber with an opening for coupling to said in-service pipeline wherein said chamber is dimensioned to house therein said blade transducer while said blade transducer is oriented in said retracted orientation wherein said retracting-reinserting shaft provides for alternately retracting into said chamber said blade transducer from said in-service pipeline through said opening to orient said blade transducer in said retracted orientation wherein said blade transducer freely pivots to orient said length dimension substantially perpendicular to a direction of flow of said medium and reinserting said blade transducer in said in-service pipeline through said opening to orient said blade transducer in said measuring orientation in said in-service pipeline wherein a drag force from said medium exerted on said blade transducer causes said blade transducer to freely pivot to orient said length dimension substantially parallel to said direction of said flow of said medium.

2. The serviceable measuring device of claim 1, wherein said chamber comprises a valve which is closable when said blade transducer is in said retracted orientation and retracted in said chamber above said valve and wherein said valve when closed closes said opening to said in-service pipeline and when said valve is opened said blade transducer is capable of being reinserted in said in-service pipeline via said retracting-reinserting shaft through said valve and said opening in said chamber to said measuring orientation.

3. The serviceable measuring device of claim 1, wherein said blade transducer comprises:

a flat and thin rectangular member with said length dimension and a width dimension and with a modified first short end and a modified second short end; and, wherein said modified first short end is curved; and, wherein said modified second short end is formed as a circular head attached to a hunched-back neck with a chest contoured to serve as a guide for use when retracting said blade transducer from said in-service pipeline; and, wherein said circular head provides a pivot means for swinging said blade transducer into said measuring orientation in said in-service pipeline or said retracted orientation.

4. The serviceable measuring device of claim 3, wherein said modified first short end is curved in the shape of a semi-circle.

5. The serviceable measuring device of claim 3, wherein said blade transducer further comprises a stop protrusion coupled to a base of said circular head wherein said stop protrusion limits the pivotal rotation of said blade transducer.

6. The serviceable measuring device of claim 3, further comprising:

a sensor coupled to said retracting-reinserting shaft;

an oblique arm coupled to said sensor wherein said oblique arm forms an oblique angle with an axis of said retracting-reinserting shaft; and a pivot rod for rotatably coupling said oblique arm to said head of said blade transducer.

7. The serviceable measuring device of claim 1, wherein said parameter is the consistency of pulp stock flow.

8. The serviceable measuring device of claim 1, wherein said parameter is the viscosity of said medium.

9. A method of inserting to a measuring state and retracting to a retracted state into and from an in-service pipeline a blade transducer of a measuring device wherein said measuring device includes a chamber and a shaft having coupled to a first distal end thereof said blade transducer wherein said in-service pipeline has flowing therein a medium, said method of inserting to said measuring state and retracting to said retracted state said blade transducer comprising the steps of:

a) longitudinally moving said shaft in a first direction in said chamber;

b) simultaneously with a), rotating said blade transducer from a first orientation to a second orientation, freely, about said first distal end of said shaft;

c) orienting freely said blade transducer in the flow of said medium via a drag force from said medium to said second orientation wherein, when said blade transducer is in said second orientation, said blade transducer is in said measuring state;

d) longitudinally moving said shaft in a second direction in said chamber; and, e) simultaneously with d), rotating said blade transducer from the second orientation, freely, about said first distal end of said shaft, to said first orientation wherein when said blade transducer is in said first orientation said blade transducer is in said retracted state out of said in-service pipeline.

10. The method of claim 9, wherein the step of c) further comprises the step of c1) measuring a parameter of said medium when said blade transducer is in said second orientation.

11. The method of claim 9, further comprises the step of before the step of a) opening a valve coupled to said chamber; and, wherein during the step of a) said blade transducer passes through said valve when opened.

12. The method of claim 9, further comprising the step of:

f) after the step of e) closing a valve coupled to said chamber;

g) removing said blade transducer from said chamber; and, h) servicing said blade transducer.

\* \* \* \* \*

UNITED STATES PATENT AND TRADEMARK OFFICE
CERTIFICATE OF CORRECTION

PATENT NO   : 5,962,795
DATED       : Oct. 5, 1999
INVENTOR(S) : Dale J. Lambert It is certified that error appears in the above-identified patent and that said Letters Patent are hereby corrected as shown below:

Column 3, Line 4, "as desired" should read --as desired.--; Lines 64, "in a slurry A wood" should read --in a slurry. A wood--. Column 8, Line 18, "present;" should read --present invention;--; Line 38, "illustrates an rear" should read --illustrates a rear--; Line 40, "illustrates an top" should read --illustrates a top--; Line 42, "illustrates an cross-sectional" should read --illustrates a cross-sectional--; Line 45, the word "and" should be deleted; Line 47, "the present invention;" should read --the present invention; and--. Column 13, Line 6 and Line 7, the space between "Referring now to" and "FIGS. 9a" should be deleted. Column 14, Line 20, "In operation, the medium" should begin a new paragraph. Claim 12, Line 1, "the step of:" should read --the steps of:--.

Signed and Sealed this

Fifteenth Day of May, 2001

Attest:

NICHOLAS P. GODICI

Attesting Officer

Acting Director of the United States Patent and Trademark Office